US011357976B2

United States Patent
Zaidi et al.

(10) Patent No.: US 11,357,976 B2
(45) Date of Patent: Jun. 14, 2022

(54) ELECTRODE DEVICES FOR NEUROSTIMULATION

(71) Applicant: GALVANI BIOELECTRONICS LIMITED, Brentford (GB)

(72) Inventors: Faisal Zaidi, Brentford (GB); Sebastien Ouchouche, Brentford (GB)

(73) Assignee: Galvani Bioelectronics Limited, Brentford (GB)

( * ) Notice: Subject to any disclaimer, the term of this patent is extended or adjusted under 35 U.S.C. 154(b) by 62 days.

(21) Appl. No.: 16/634,632

(22) PCT Filed: Jul. 23, 2018

(86) PCT No.: PCT/GB2018/052074
§ 371 (c)(1),
(2) Date: Jan. 28, 2020

(87) PCT Pub. No.: WO2019/020983
PCT Pub. Date: Jan. 31, 2019

(65) Prior Publication Data
US 2021/0085964 A1 Mar. 25, 2021

Related U.S. Application Data

(60) Provisional application No. 62/538,410, filed on Jul. 28, 2017.

(51) Int. Cl.
*A61N 1/05* (2006.01)
*A61N 1/36* (2006.01)

(52) U.S. Cl.
CPC .................................. *A61N 1/0556* (2013.01)

(58) Field of Classification Search
CPC .. A61N 1/0551; A61N 1/0556; A61N 1/0558; A61N 1/3605; A61N 1/3606; A61N 1/375
See application file for complete search history.

(56) References Cited

U.S. PATENT DOCUMENTS

| 5,003,992 A | 4/1991 | Holleman et al. |
| 5,400,784 A * | 3/1995 | Durand ................ A61N 1/0556 29/825 |

(Continued)

FOREIGN PATENT DOCUMENTS

| EP | 0865800 A2 | 9/1998 |
| EP | 1935448 A1 | 6/2008 |

(Continued)

OTHER PUBLICATIONS

International Search Report for Application No. PCT/GB2018/052074, dated Nov. 6, 2018, 2 pages.

(Continued)

*Primary Examiner* — Carl H Layno
*Assistant Examiner* — Anh-Khoa N Dinh
(74) *Attorney, Agent, or Firm* — Patterson Thuente Pedersen P.A.

(57) ABSTRACT

An extravascular neural interface is disclosed including a device containing electrodes for neurostimulation of a vessel. The devices are housed in flexible substrates forming two flaps, an inner flap having a spinal portion for routing leads/conductors into the device for connection to the electrodes and an outer flap that overlaps the inner flap. The inner flap supports and positions the electrodes to be inward facing, i.e., extravascular designs. The electrodes may be circular or elliptical and include a plurality of wings for securing the electrodes within a flap.

20 Claims, 5 Drawing Sheets

(56) References Cited

U.S. PATENT DOCUMENTS

| | | | |
|---|---|---|---|
| 6,292,703 B1 | 9/2001 | Meier et al. | |
| 8,155,757 B1 | 4/2012 | Neisz et al. | |
| 8,515,520 B2 | 8/2013 | Brunnett et al. | |
| 2006/0041277 A1* | 2/2006 | Deem | A61N 1/36128 607/3 |
| 2006/0271137 A1* | 11/2006 | Stanton-Hicks | A61N 1/0551 607/118 |
| 2008/0103545 A1* | 5/2008 | Bolea | A61N 1/37229 607/42 |
| 2010/0268311 A1 | 10/2010 | Cardinal et al. | |
| 2014/0188202 A1 | 7/2014 | Zarembo et al. | |

FOREIGN PATENT DOCUMENTS

| | | |
|---|---|---|
| WO | WO-2008048471 A2 | 4/2008 |
| WO | WO-2009135075 A1 | 11/2009 |
| WO | WO-2014018092 A1 | 1/2014 |

OTHER PUBLICATIONS

International Search Report for Application No. PCT/GB2018/052077, dated Oct. 15, 2018, 2 pages.

* cited by examiner

FIG. 3A
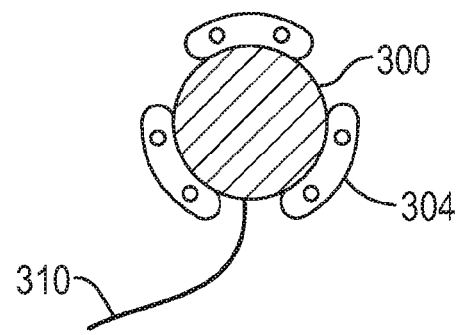
FIG. 3B
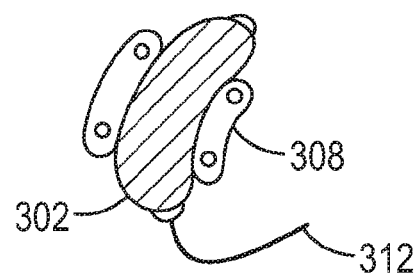
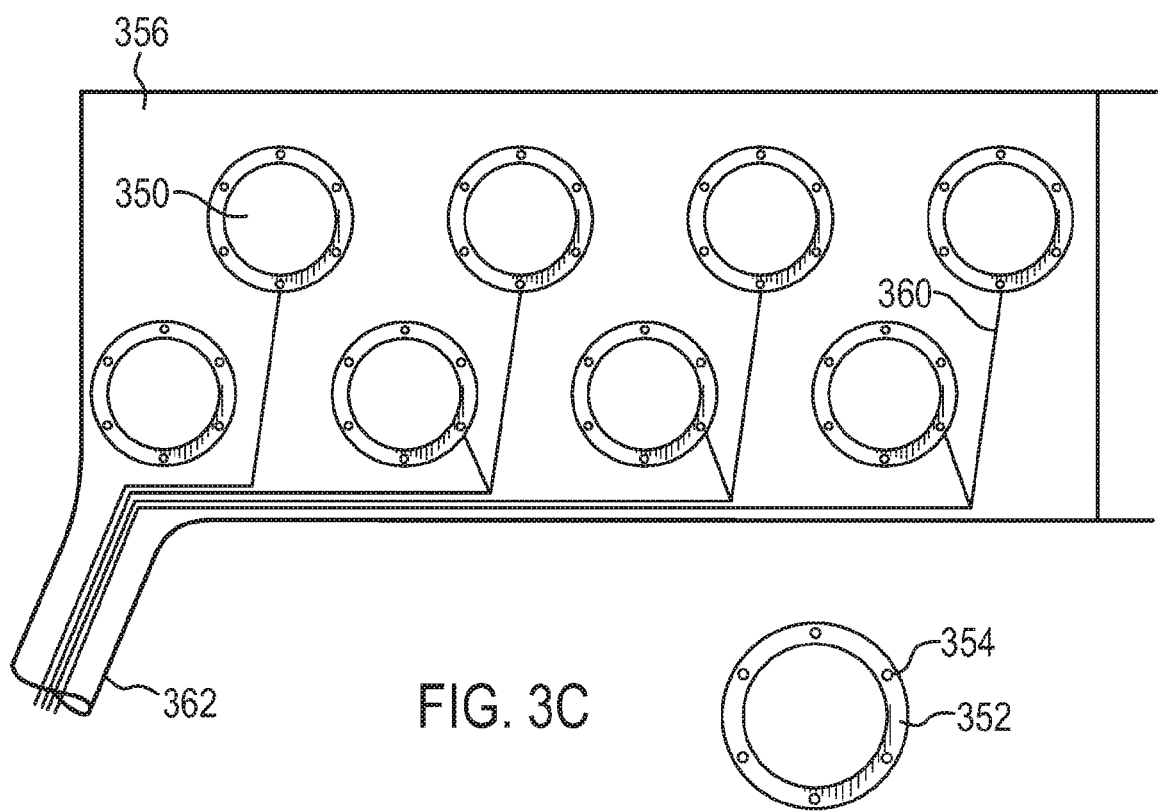
FIG. 3C

ELECTRODE DEVICES FOR NEUROSTIMULATION

PRIORITY CLAIM

The present application is a National Phase entry of PCT Application No. PCT/GB2018/052074, filed Jul. 23, 2018, which claims priority from U.S. Provisional Application No. 62/538,410, filed Jul. 28, 2017, each of which is hereby fully incorporated herein by reference.

BRIEF DESCRIPTION

The present disclosure is related to embodiments of extravascular devices containing electrodes for neurostimulation of a target vessel. The devices are housed in flexible substrates forming two flaps, an inner flap having a spinal portion for routing leads/conductors into the device for connection to the electrodes and an outer flap that overlaps the inner flap. The inner flap supports and positions the electrodes to be inward facing, i.e., extravascular designs. The electrodes may be circular or elliptical and include a plurality of wings for securing the electrodes within a flap.

CROSS-REFERENCES TO RELATED APPLICATIONS

Not Applicable.

STATEMENT AS TO THE RIGHTS TO INVENTIONS MADE UNDER FEDERALLY SPONSORED RESEARCH OR DEVELOPMENT

Not Applicable.

BACKGROUND

Electrical devices of various shapes and sizes including one or more electrodes have been used for neurostimulation of target anatomy for years. U.S. Pat. No. 7,231,260 discloses an intravascular device that includes a single flap with a few electrodes that can be collapsed (rolled up) to fit within a catheter for implantation, and which expands outside of the catheter to cover a portion (less than 360 degrees) of the inside walls of a target vessel. To keep the flap in place against the target vessel wall, the flap itself may be an arcuate resilient spring formed of polyimide, polytetrafluoroethylene, fluorinated ethylene propylene, polyethylene or silicone, or include a plurality of resilient spring loops mounted to the flap to apply pressure against an opposing wall, thereby pushing the flap against the opposing target vessel wall.

The above illustrates existing designs with flaps that cover a portion of the interior circumference of a target vessel. Such designs fail to cover the entire circumference of the target vessel and lack radial flexibility and self-sizing capabilities relative to the entire target vessel. If the target vessel is excessively compressed by the device, nerve damage may result from the decreased blood flow and constricted nerve fibers. Temporary swelling of the target vessel caused by the trauma of the surgical positioning of the device can exacerbate such nerve damage. In contrast, loose fitting devices can result in poor electrical contact and low treatment efficiency, which can further degrade over times as a result of ingrowth of connective tissue between the target vessel and the device.

In Zaidi F. N., Meadows P., Jacobowitz O., Davidson T. M., 2012, *Tongue Anatomy and Physiology, the Scientific Basis for a Novel Targeted Neurostimulation System Designed for the Treatment of Obstructive Sleep Apnea*, Neuromodulation 2013; 16: 376-386, a six contact self-sizing, spiral cuff electrode is briefly described in which six independent current sources are used to separately control six separate electrodes in the cuff electrode. The electrodes are arranged in the material of the cuff and aligned so that a spiral circumference of the nerve is contacted by an electrode. Each of the electrodes includes one or more wings around a periphery that may be used to secure the electrodes within the cuff material. U.S. Pat. Nos. 8,886,322 and 9,579,505 and U.S. Pat. App. Pub. No. US 2014/0236255 A1 further illustrate and describe the same overlapping cuff design for treatment of the Hypoglossal nerve, but which does not address all of the limitations of conventional devices.

Conventional helical or serpentine electrode devices further address some of the limitations of conventional rigid cuff-like and cage-like devices, such as permitting some radial expansion that helps with post-positioning edema or swelling of the target vessel, more fluid exchange with surrounding tissue, better electrical contact, and reduced growth of connective tissue. Helical or serpentine devices, however, require a complex positioning that requires significant dissection and nerve manipulation in order to wind the helix around the nerve at least two times (passes). Positioning of such devices also requires mobilization of a large portion of the nerve because the cathode and anode electrodes are typically positioned by their own device.

Cuff-like devices require electrodes that provide maximum electrode coverage while being radially compliant. The term "compliant" as used herein refers to the amount of flexibility and/or give that an object might have and particularly in reference to its ability to interact with other objects. For example, when a first object puts physical pressure on a second object intended to work with the first object, the second object is compliant if it is capable of adjusting to that physical pressure, while continuing to perform its intended function. Conventional electrodes used for this purpose include very thin metal sheet electrodes, segmented metal contacts, and thin-film based electrodes. Thin metal sheets can be difficult to connect to leads, provide limited radial compliance and are prone to breakage if excessive stress is applied to the cuff (i.e., from opening and closing). Segmented contact electrodes increase the complexity of manufacturing the cuff and provide limited electrode coverage. Thin film based electrodes can also be difficult to interconnect to lease and are prone to delamination.

BRIEF DESCRIPTION OF THE SEVERAL VIEWS OF THE DRAWING

FIG. 3A, FIG. 3B and FIG. 3C illustrate a variety of different electrodes with extending wings or spikes or protruding bites for enabling the electrodes to be embedded between sheets of the flap structure;

DETAILED DESCRIPTION

The present disclosure is related to embodiments of extravascular devices containing electrodes for neurostimulation of a target vessel. The extravascular devices may be selectively stimulating devices for neurostimulation of the vessel. The devices are housed in flexible substrates forming two flaps, an inner flap having a spinal portion for routing leads/conductors into the device for connection to the electrodes and an outer flap that overlaps the inner flap. The inner flap supports and positions the electrodes to be inward facing, i.e., extravascular designs. The electrodes may be circular or elliptical or elongated and include a plurality of wings/bites/protrusions for securing the electrodes within a flap.

In the present disclosure, a vessel refers to a vessel and a nerve (or nerves) that travels along with the vessel. The vessel may be an artery (or arteries) and/or a vein (or veins) and/or a lymph vessel (or lymph vessels). A nerve that travels along a vessel may be a nerve that is adjacent to the vessel or a nerve that is in the vicinity of the vessel.

Figure 1A:
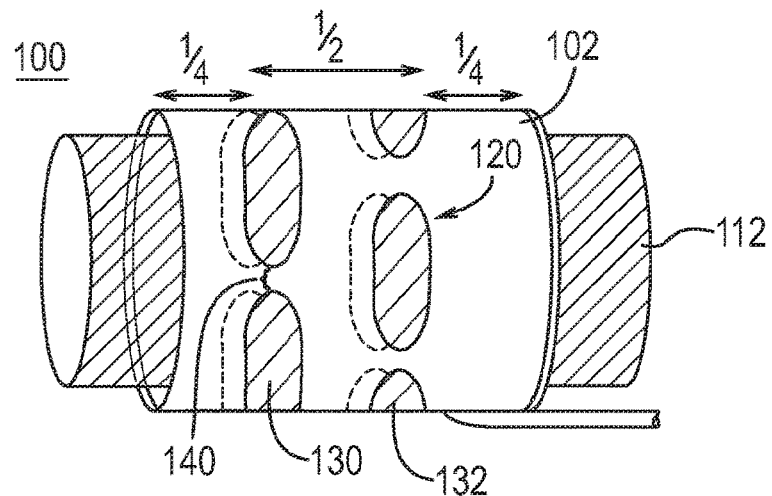
FIG. 1A is a perspective view of an embodiment of an extravascular neural interface device including a flexible overlapping flap structure holding and positioning a plurality of elongated elliptical (curved) electrodes.
Figure 1B:
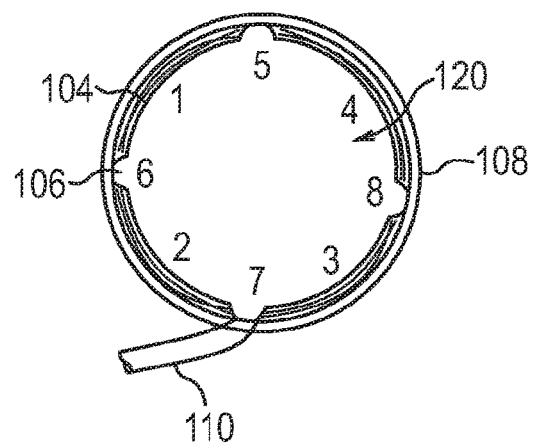
FIG. 1B is an end view of the embodiment of FIG. 1A.

In the present disclosure, a target vessel may be a target vessel that includes a nerve (or nerves) that travels along with the vessel. The target vessel may be an artery (or arteries), and/or a vein (or veins), and/or a lymph vessel (or lymph vessels). An embodiment of a bi-polar, extravascular neural interface 100 in accordance with the present disclosure is illustrated in FIG. 1A and FIG. 1B. The neural interface 100 may comprise a self-sizing cuff 102 that is formed of a supporting substrate manufactured of silicone or a similar flexible substance, such as styrene isoprene butadiene (SIBS), polyamide, parylene, liquid-crystal polymer (LCP), polytetrafluoroethylene (PTFE), polyethylene (PE), polypropylene (PP), fluorinated ethylene propylene (FEP), ethylene-tetrafluoroethylene (ETFE), polyurethane, or another biocompatible polymer. As shown in FIG. 1B, the cuff 102 may include an inner flap 104, with a tapering end 106 and an outer flap 108.

The inner flap 104 may include a spinal portion or spine 110 that houses leads or conductors for each of the electrodes. The flaps may be positioned orthogonal to the length of the target vessel (not shown) around which the flaps may be ultimately wrapped or may be positioned at an angle, such as 45 degrees relative to the length. The inner flap 104 may be wrapped around the target vessel and the outer flap 108 may then be wrapped around the inner flap 104.

Figure 2:
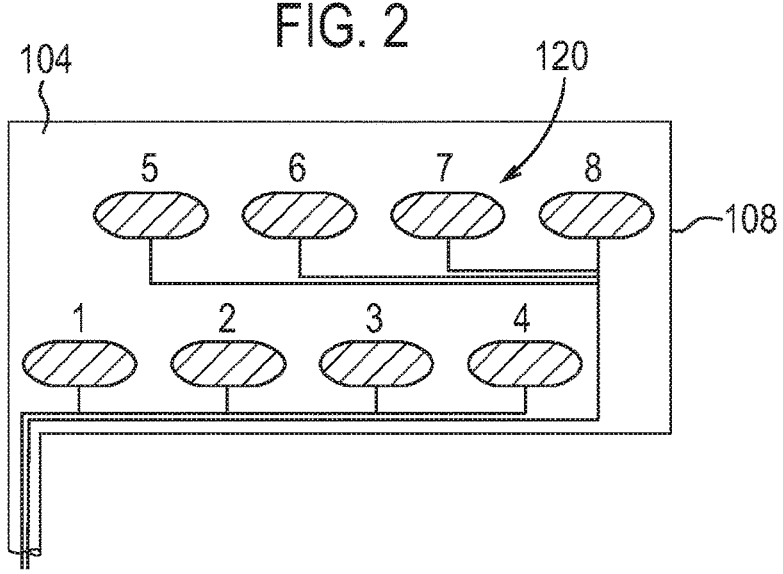
FIG. 2 is a side view of the embodiment of FIG. 1A.

Housed and positioned within the inner flap 104 may be a series of 8 or more substantially elliptical curved electrodes 120 that may be staggered so as to form a circular pattern around the target vessel when the neural interface 100 has been positioned and closed around the target vessel. For example, FIG. 2 illustrates the series of electrodes 120 labeled from 1 to 8, with one column of electrodes (1-4) substantially opposite, yet offset from, a second column of electrodes (5-8), while FIG. 1B illustrates the resulting arrangement of the 8 electrodes from an end view. FIG. 1A illustrates the series of electrodes 120 positioned to form a staggered circular ring pattern around the target vessel 112. FIG. 2 illustrates the electrodes 120 when the inner flap 104 and the outer flap 108 are laid on a flat surface, such that once electrodes (1-4) are rolled over electrodes (5-8), the 8 electrodes will be arranged as shown in FIG. 1A.

The series of electrodes 120 may be positioned in a selective or non-selective polarity layout and may include a positive left hand spiral column and a negative right hand spiral column, or may be formed in any other combination or arrangement. The electrodes 120 may be platinum or platinum alloy electrodes (or electrode arrays). The electrodes 120 may be of a conventional type and wired to a controller through conventional conductors, such as 35N LT® DFT (Drawn Filled Tubing) with a 28% Ag core, in a stranded cable configuration or in a multi-filar coil configuration. The conductors are housed in spinal portion or spine 110.

The "segmented" electrode designs may provide better mechanical compliance, create the possibility of surface features, i.e., protruding electrodes, and make it possible to control each electrode individually (i.e., current steering). For example, connecting individual electrodes or different arrays of electrodes to different conductors may enable selective stimulation of the target vessel by individually controlling each connected device. Individual electrodes, if wired separately, may be selected and activated for power/current grading of a stimulation field of the target vessel. In addition, the polarity of the electrodes may be controlled independently. For example, all of the electrodes in a first row of electrodes 130 may have a negative polarity while all of the electrodes in a second row of electrodes 132 may have a positive polarity, or the negative and positive polarity may be mixed in both of the rows of electrodes 130 and 132. In other words, the polarity of any electrode can be determined by a controller (not shown) providing power to the electrode and is not necessarily dependent on a mechanical structure of an electrode to determine that electrode's polarity. Nevertheless, the electrodes can be configured to have a specific polarity and configured for that polarity to be changed. For example, an electrode could be configured to have a selective negative polarity, i.e., negative polarity is selected, and then be configured, at a later point in time, to have a selective positive polarity.

The electrodes 120 may also be positioned in an overlapping fashion, such that no electrical transverse gaps are created between the electrodes in rows 130 and 132. For example, in FIG. 1A, the electrodes in the row 130 may be offset from the electrodes in the row 132 so as to cover at least a helical turn of the electrodes 130 when the neural interface 100 is positioned around the target vessel, which also prevents any transverse gaps between the rows. An "electrical transverse gap" refers to any gap between electrodes which extends along the longitudinal axis of the spiral neural interface, the longitudinal axis of the neural interface corresponding to a direction along the target vessel. In other words, an electrical transverse gap is formed on a circumference of the neural interface (the circumference formed when the neural interface is positioned on the target vessel) when the electrodes are aligned so that there is point along a line following the length of the interface where an electrode is not encountered. If a first set of segmented electrodes, each with a gap between it and any neighboring electrode, are positioned around the circumference, in order to eliminate any electrical transverse gap in the neural interface, a second set of segmented electrodes, each with a gap between it and any neighboring electrode, would need to be positioned next to the first set, along the length of the target vessel, such that each electrode in the second set is positioned adjacent to a gap formed in the first set, and vice versa, such that at no point along a line following the length of the target vessel where the neural interface is positioned, would at least one electrode would not cross the line. If the gaps between electrodes were bigger than the size of an electrode, additional sets of segmented electrodes could be utilized with each set staggered so as to prevent an electrical transverse gaps. A physical transverse gap refers to any gap between electrodes which extends over a portion of the length of the inner flap.

Aligning individual electrodes or arrays of electrodes so as to remove electrical transverse gaps, say between two rows of electrodes or some other arrangement, may insure complete electrical coverage (360° circumferential coverage) of the target vessel over a length of the target vessel. For example, as illustrated in FIG. 1A, a total of 8 coiled platinum electrode rows or strips may be utilized in each neural interface. Neural interface 100 may also be configured for intravascular applications by locating the electrodes along exterior surfaces of the neural interface 100.

Other electrode shapes may also be used. For example, each of the substantially circular electrodes 300 and the substantially elliptical curved electrodes 302 are further illustrated in FIG. 3A and FIG. 3B, respectively. As illustrated in FIG. 3A, each electrode 300 may include a plurality of wings 304 that may include a number of holes/bites/protrusions in each wing. The inner flap 104 may be manufactured from sheets of substrate material. The electrode 300 may be connected to lead wired 310 and positioned on a first sheet of the inner flap 104. Glue or silicone may be used to fill the holes of the wings 304 before a second sheet is applied over the top. In an embodiment, the electrodes 300 may be positioned on a sheet and have a second sheet reflowed over the top to fill the holes of the wings. Sheet material covering the electrodes may be laser ablated, if necessary, to expose the surface of the electrode. In an embodiment, the first or second sheet may have holes preformed in the sheet to indicate the position of each electrode and to expose the surface of the electrode, as necessary, relative to the second sheet.

As illustrated in FIG. 3B, each electrode 302 may include a plurality of wings 308 that may include a number of holes/bites/protrusion in each wing. The inner flap 104 may be manufactured from sheets of substrate material. The electrode 302 may be connected to lead wired 312 and positioned on a first sheet of the inner flap 104. Glue or silicone may be used to fill the holes of the wings 308 before a second sheet is applied over the top. In an embodiment, the electrodes 302 may be positioned on a sheet and have a second sheet reflowed over the top to fill the holes of the wings. Sheet material covering the electrodes may be laser ablated, if necessary, to expose the surface of the electrode. In an embodiment, the first or second sheet may have holes preformed in the sheet to indicate the position of each electrode and to expose the surface of the electrode, as necessary, relative to the second sheet.

As illustrated in FIG. 3C, each substantially circular electrode 350 has a substantially circular ring 352, essentially a continuous wing, attached to and positioned around the electrode 350. The ring 352 includes a number of holes 354 around the ring 352, which may be filled with glue or silicone, as discussed above, in order to hold the electrode 350 in position within the inner flap 356. As illustrated in FIG. 24 and FIG. 3C, the lead wires from each electrode may be routed through the sheets of the inner flap to a spinal portion or spine. For example, as shown in FIG. 3C, the leads 360 of each electrode 350 is routed in-between the sheets of the inner flap 356 to spinal portion or spine 362 and then away from the device to a controller (not shown).

Figure 4A:
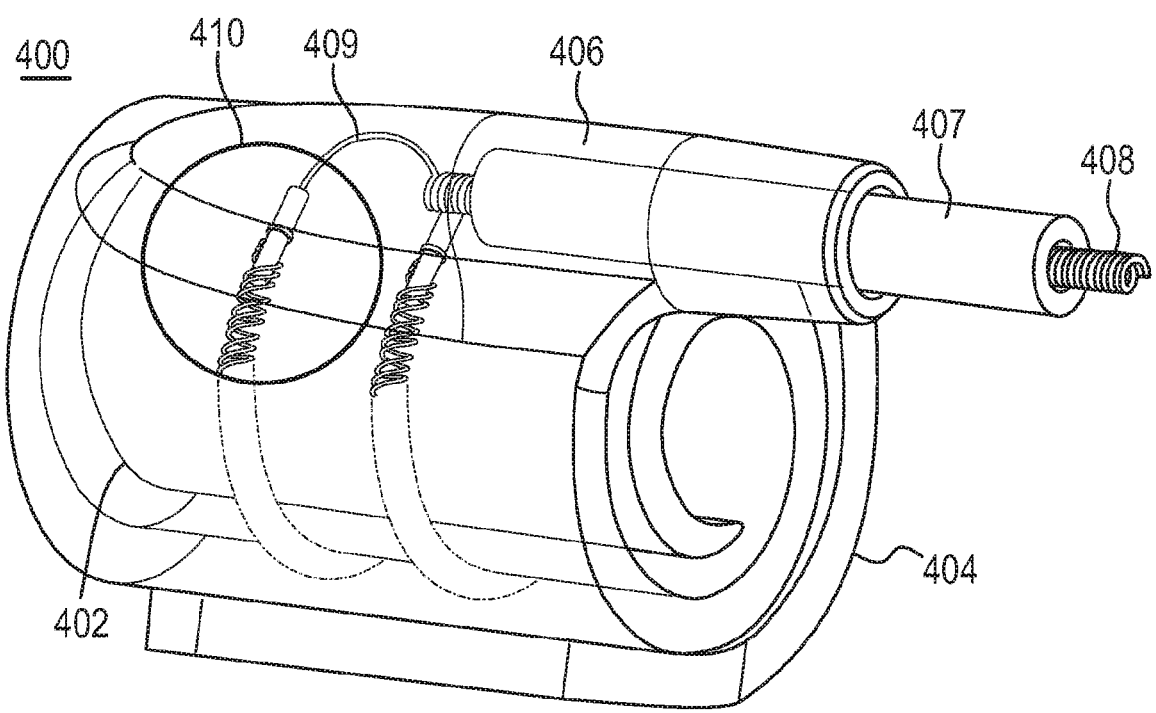
FIG. 4A is a perspective view of an embodiment of an extravascular neural interface device including a flexible overlapping flap structure holding and positioning coil electrodes.
Figure 4B:
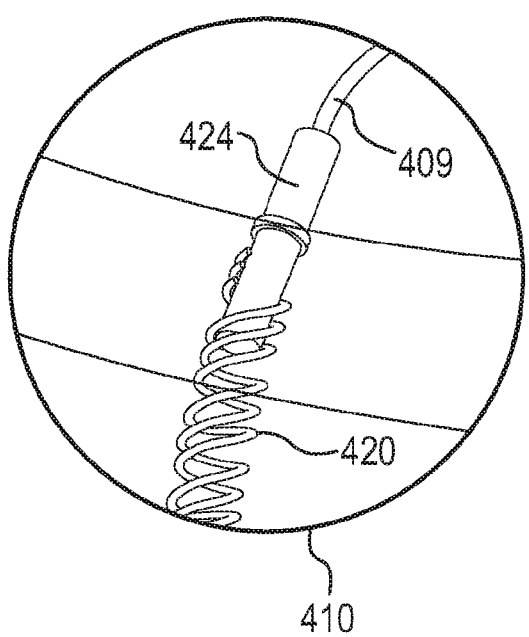
FIG. 4B is a detailed view of the interface connecting the coil electrode to the conductor.

The overlapping flaps of the cuff of the neural interface may also be manufactured with coil electrodes, further illustrated with reference. FIG. 4A illustrates a cuff 400 of an extravascular neural interface device similar to those already described above. For example, the cuff 400 may include an inner flap 402 and an outer flap 404 connected to a spinal portion or spine 406. The spine 406 may include a silicone tubing 407 through which the leads/conductors of the electrodes may be housed and routed, with the individual leads 409 for each electrode exiting a distal end of the tubing 407. The circled area 410 of FIG. 4A is further illustrated in FIG. 4B. As shown therein, the lead 409 may by connected to the coil electrode 420 by a crimp/weld sleeve 424.

Figure 5:
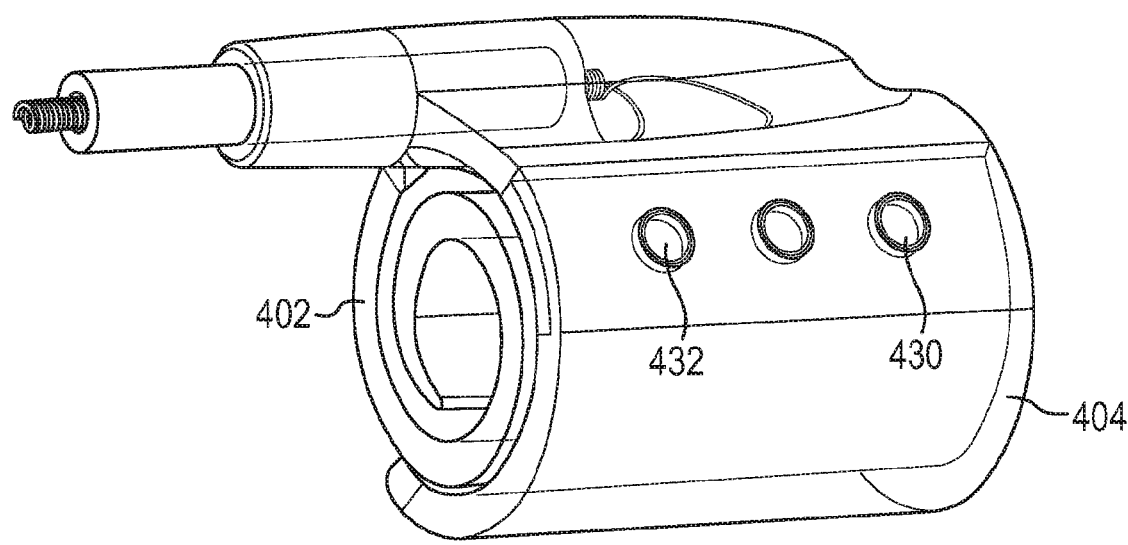
FIG. 5 is a perspective view of the embodiment of FIG. 4A further illustrating the outer flap of the neural interface device.

The electrode 420, sleeve 424, conductor 408, lead 409 and tubing 407 may be preassembled and positioned within a mold prior to formation of the remainder of the cuff 400. Once those components are positioned in the mold, the inner flap 402 and the spinal portion or spine 406 may be molded over those components. In an embodiment, inner flap 402 and spinal portion or spine 406 may be molded at a shore hardness of approximately 20 A so as to be compliant and self-sizing. In an embodiment, after molding the inner flap 402, the outer flap 404, which is further illustrated in FIG. 5, may be molded at a shore hardness of approximately 75 A. The term "hardness" generally refers to a measure of how resistant solid matter is to permanent shape change when a compressive force is applied, which hardness of the material may be measured with a durometer As shown in FIG. 5, the outer flap 404 may include a set of holes 430 through which protrusions 432 formed in the molding of inner flap 402 may be inserted. In such an embodiment, a portion of the inner flap 402, sufficient to support the protrusions 432, may be formed on a first side of the spinal portion/spine 406 while the remainder of the inner flap is formed on the second (opposite) side of the spinal portion/spine 406. The outer flap 404 may then be formed on the first side over the portion of the inner flap 402 on that same side, with the protrusion extending through the holes 430, which is configured to enable the inner flap 402 to be mechanically locked to the more rigid outer flab 404.

Figure 6:
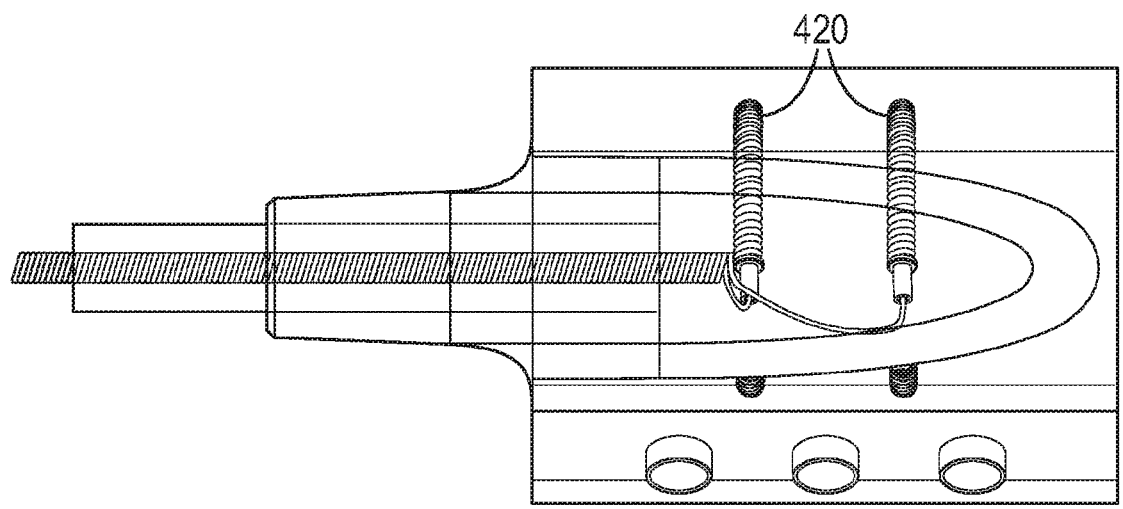
FIG. 6 is a top view of the embodiment of FIG. 5.
Figure 7A:
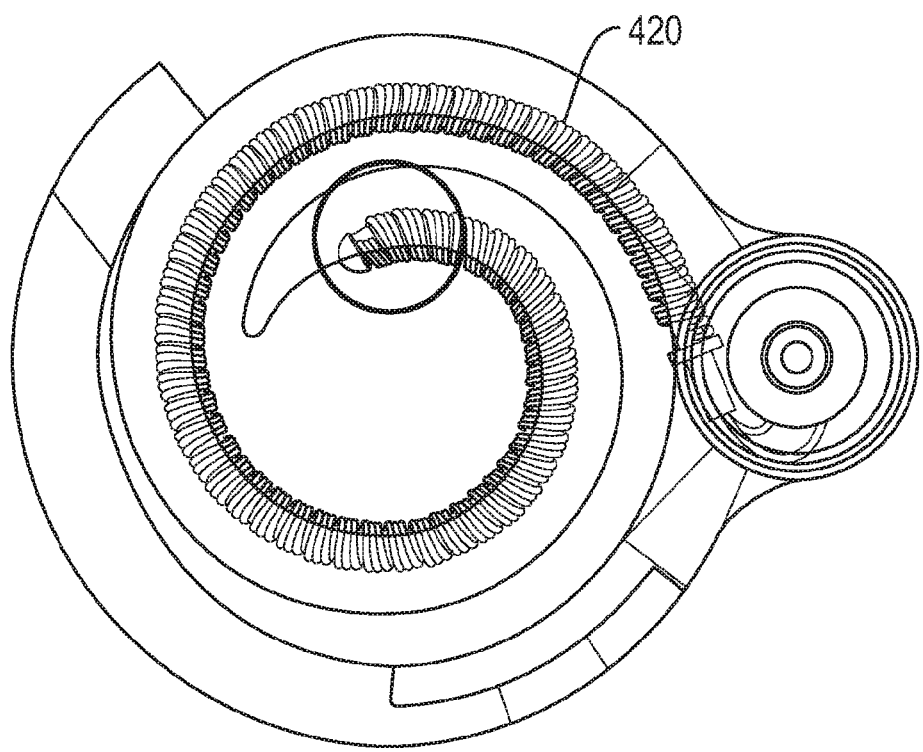
FIG. 7A illustrates a side view of the embodiment of FIG. 6.

As further illustrated in FIG. 6, there may be multiple electrodes 420, although only two are shown therein, connected to the lead wires 409 of the conductor 408. The electrodes 420 may be positioned in a central area of the cuff 400 and spaced appropriately from one another. As further Illustrated in FIG. 7A, the electrode 420 may be exposed at the interior surface of the inner flap 402 (i.e., only partially embedded, hence slightly protruding) so as to make good contact with the surface of the target vessel and largely follow the along the width of the inner flap 402. In addition, the topology of the surface of the electrode 420 leads to a greater active surface of the electrode 420 compared to conventional flat electrodes. For instance, for the same footprint, a coil electrode can provide two times more exposed electrode surface.

Figure 7B:
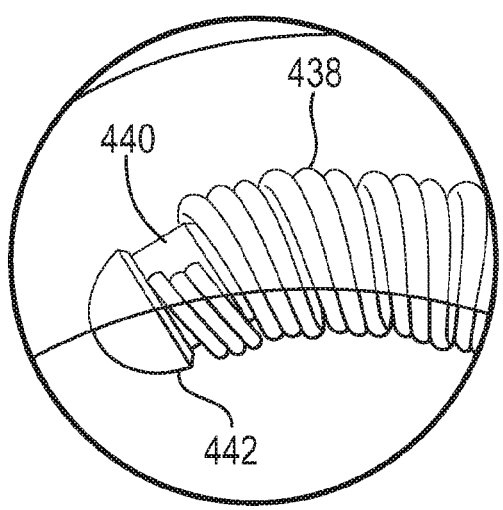
FIG. 7B is a detailed view of the distal end of the coil electrode of FIG. 7A.

The electrodes 420, as illustrated in FIG. 7B, may include one or more filars 438 wrapped in a coil around a central portion 440 and terminated at a laser welded plug 442. The number of filars 438 involves a trade-off between the electrode compliance and electrical resistance of the electrode 406. Increasing the number of filars 438 decreases the radial compliance of the electrode 406 while decreasing the electrode's electrical resistance. The coil electrode may be a bipolar cuff electrode.

The compliancy of inner flap 402, which may be molded from silicone or a similar material, is configured such as to allow the inner flap 402 to self-size to target vessels of varying radial width, yet maintain close to 360 degree coverage of the surface of the target vessel. The material used to mold the inner flap 402 may be doped with a steroid drug, such as dexamethasone. In an embodiment, outer surface of the cuff 00 may also, or alternatively, be coated with a hydrophilic polymer, such as poly-2-hydrohyethyl-methacrylate (pHEMA).

The resulting cuff 400 provides excellent radial compliance because the coil electrode 406 is designed to be as compliant as the material of the inner flap 402, thereby reducing flex fatigue and a tendency to kink or wrinkle as may be the case with conventional electrodes. In addition the coil electrode 406 may stretch and therefore provide a lower radial force, thereby reducing pressure on the nerves of the target vessel. At the same time, the extended length of the coil electrode 406 and its position within the inner flap 402 of the cuff 400 maximize circumferential coverage and active surface coverage. This reduces the need to segment the electrodes in order to increase compliance. Finally, the conductors can be easily connected to the electrodes and is easy to manufacture.

The word "substantially" does not exclude "completely" e.g. a composition which is "substantially free" from Y may be completely free from Y. Where necessary, the word "substantially" may be omitted from the definition of the disclosure. For example, features arranged substantially opposite may be opposite. Furthermore, the substantially circular electrodes and the substantially elliptical electrodes may be circular electrodes and elliptical electrodes respectively.

In an embodiment, a neural interface comprises a spinal portion configured to house electrical leads for one or more electrodes and provide a supporting structure; a flexible inner flap connected to the spinal portion and configured to house and position the one or more electrodes around a target vessel, wherein the one or more electrodes are arranged so as to form no electrical transverse gap between electrodes over at least a 360 degree turn around an exterior surface of the target vessel when positioned around the target vessel; and an outer flap connected the flexible inner flap and configured to overlap the flexible inner flap.

In the embodiment of the neural interface, wherein the one or more electrodes includes a series of electrodes, wherein each electrode among the series of electrodes is connected to a separate electrical lead.

In the embodiment of the neural interface, wherein the series of electrodes includes a first set of four or more substantially elliptical curved electrodes positioned at a 45 degree angle relative to a length of the target vessel and a second set of four or more substantially elliptical curved electrodes positioned at a 45 degree angle relative to the length of the target vessel.

In the embodiment of the neural interface, wherein the first set of electrodes is configured to have a positive polarity and the second set of electrodes is configured to have a negative polarity.

In the embodiment of the neural interface, wherein the first set of electrodes is positioned substantially opposite the second set of electrodes relative to the target vessel.

In the embodiment of the neural interface, wherein a polarity of each electrode is selectable and a drive current for each electrode is selectable.

In the embodiment of the neural interface, wherein the series of electrodes includes a first set of electrodes positioned orthogonal to a length of the target vessel and a second set of electrodes positioned orthogonal the length of the target vessel.

In the embodiment of the neural interface, wherein the first set of electrodes has a positive polarity and the second set of electrodes has a negative polarity.

In the embodiment of the neural interface, wherein a polarity of each electrode is selectable and a current intensity for achieving the current gradient for each electrode is selectable.

In the embodiment of the neural interface, wherein the first set of electrodes are parallel to the second set of electrodes, and wherein the first set of electrodes is offset from the second set of electrodes, such that a center of at least one electrode in the second set of electrodes is positioned between two electrodes of the first set of electrodes.

In the embodiment of the neural interface, wherein electrodes in the series of electrodes are substantially circular.

In the embodiment of the neural interface, wherein electrode in the series of electrodes are substantially elliptical.

In the embodiment of the neural interface, wherein the one or more electrodes include one or more wings connected to the one or more electrodes, wherein one or more protrusions/bites/holes are formed in the wings, and wherein the one or more bites/holes are configured to be filled with a material to attach the one or more wings to the flexible inner flap.

In the embodiment of the neural interface, wherein the flexible inner flap is formed of at least two sheets, wherein the one or more wings are affixed to a first sheet among the at least two sheets and covered with a second sheet among the at least two sheets.

In the embodiment of the neural interface, wherein openings are formed in the second sheet to expose the one or more electrodes.

In the embodiment of the neural interface, wherein glue or silicone affixes the one or more wings to the first sheet.

In the embodiment of the neural interface, wherein the one or more wings includes a plurality of segmented wings.

In the embodiment of the neural interface, wherein flexible inner flap and the outer flap are formed from a silicone-based material.

In the embodiment of the neural interface, wherein the silicone-based material is doped with a steroid drug.

In the embodiment of the neural interface, wherein the silicone-based material is coated with a hydrophilic polymer.

The embodiments of the present disclosure, while illustrated and described in terms of various embodiments, is not limited to the particular description contained in this specification. Additional alternative or equivalent components and elements may be readily used to practice the present disclosure.

What is claimed is:
1. A neural interface, comprising:
a spinal portion configured to house electrical leads for a one or more electrodes and provide a supporting structure;
a flexible inner flap connected to the spinal portion and configured to house and position the one or more electrodes around a target vessel, wherein the one or more electrodes includes a first set of electrodes and a second set of electrodes;

further wherein the first set of electrodes are arranged parallel to the second set of electrodes, and wherein the first set of electrodes is offset from the second set of electrodes, such that a center of at least one electrode in the second set of electrodes is positioned between two electrodes of the first set of electrodes, the first and second sets of electrodes further arranged so as to form no electrical transverse gap between electrodes over at least a 360 degree turn around an exterior surface of the target vessel when positioned around the target vessel.

2. The neural interface of claim 1, wherein the first and second sets include a series of electrodes, wherein each electrode among the series of electrodes is connected to a separate electrical lead.

3. The neural interface of claim 2 wherein the first set comprises four or more substantially elliptical curved electrodes positioned at a 45 degree angle relative to a length of the target vessel and the second set comprises four or more substantially elliptical curved electrodes positioned at a 45 degree angle relative to the length of the target vessel.

4. The neural interface of claim 3, wherein the first set of electrodes is configured to have a positive polarity and the second set of electrodes is configured to have a negative polarity.

5. The neural interface of claim 3, wherein the first set of electrodes is positioned substantially opposite the second set of electrodes relative to the target vessel.

6. The neural interface of claim 3, wherein a polarity of each electrode is selectable and a drive current for each electrode is selectable.

7. The neural interface of claim 2, wherein the first set of electrodes is positioned orthogonal to a length of the target vessel and the second set of electrodes is positioned orthogonal the length of the target vessel.

8. The neural interface of claim 7, wherein the first set of electrodes has a positive polarity and the second set of electrodes has a negative polarity.

9. The neural interface of claim 7, wherein a polarity of each electrode is selectable and a current intensity for achieving the current gradient for each electrode is selectable.

10. The neural interface of claim 7, wherein electrodes in the series of electrodes are substantially circular.

11. The neural interface of claim 7, wherein electrode in the series of electrodes are substantially elliptical.

12. The neural interface of claim 1, wherein the one or more electrodes include one or more wings connected to the one or more electrodes, wherein one or more protrusions/bites/holes are formed in the wings, and wherein the one or more bites/holes are configured to be filled with a material to attach the one or more wings to the flexible inner flap.

13. The neural interface of claim 12, wherein the flexible inner flap is formed of at least two sheets, wherein the one or more wings are affixed to a first sheet among the at least two sheets and covered with a second sheet among the at least two sheets.

14. The neural interface of claim 13, wherein openings are formed in the second sheet to expose the one or more electrodes.

15. The neural interface of claim 13, wherein glue or silicone affixes the one or more wings to the first sheet.

16. The neural interface of claim 12, wherein the one or more wings includes a plurality of segmented wings.

17. The neural interface of claim 1, wherein flexible inner flap and the outer flap are formed from a second silicone-based material.

18. The neural interface of claim 17, wherein the silicone-based material is doped with a steroid drug.

19. The neural interface of claim 17, wherein the silicone-based material is coated with a hydrophilic polymer.

20. A neural interface, comprising:
a spinal portion configured to house electrical leads for a one or more electrodes and provide a supporting structure;
a flexible inner flap connected to the spinal portion and configured to house and position the one or more electrodes around a target vessel, wherein the one or more electrodes are arranged so as to form no electrical transverse gap between electrodes over at least a 360 degree turn around an exterior surface of the target vessel when positioned around the target vessel; and
an outer flap connected to the spinal portion and arranged radially outward from the inner flap relative to the target vessel, the outer flap overlapping the flexible inner flap and having a shore hardness greater than the inner flap.

* * * * *